(12) United States Patent
Haubennestel et al.

(10) Patent No.: US 7,834,126 B2
(45) Date of Patent: *Nov. 16, 2010

(54) AMIDE-CONTAINING POLYMERS FOR RHEOLOGY CONTROL

(75) Inventors: Karlheinz Haubennestel, Wesel (DE); Stefan Moessmer, Wesel (DE); Ulrich Orth, Wesel (DE); Daniela Betcke, Wesel (DE)

(73) Assignee: BYK-Chemie GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/545,798

(22) Filed: Oct. 10, 2006

(65) Prior Publication Data

US 2007/0088148 A1    Apr. 19, 2007

(30) Foreign Application Priority Data

Oct. 12, 2005    (DE) .................. 10 2005 049 301

(51) Int. Cl.
*C08G 69/08* (2006.01)
(52) U.S. Cl. .................. 528/271; 528/123; 528/124; 528/142; 528/328; 428/379
(58) Field of Classification Search .................. 528/124, 528/123, 142; 524/328
See application file for complete search history.

(56) References Cited

U.S. PATENT DOCUMENTS 5,786,086 A * 7/1998 Frihart et al. ............... 428/379

2003/0065084 A1 * 4/2003 MacQueen et al. .......... 524/538
2008/0132671 A1    6/2008 Haubennestel

OTHER PUBLICATIONS

"U.S. Appl. No. 11/941,494, Non-Final Office Action mailed Jul. 30, 2009", 11 pgs.
"U.S. Appl. No. 11/941,494, Final Office Action mailed Jan. 25, 2010", 5 pgs.
"U.S. Appl. No. 11/941,494, Response filed Oct. 28, 2009 to Non Final Office Action mailed Jul. 30, 2009", 17 pgs.
"U.S. Appl. No. 11/941,494, Examiner Interview Summary mailed Jan. 26, 2010", 3 pgs.
"U.S. Appl. No. 11/941,494, Notice of Allowance mailed May 14, 2010", 7 pgs.
"U.S. Appl. No. 11/941,494, Preliminary Amendment filed Jul. 22, 2009", 6 pgs.
"U.S. Appl. No. 11/941,494, Response filed Mar. 23, 2010 to Final Office Action mailed Jan. 25, 2010", 11 pgs.

* cited by examiner

*Primary Examiner*—James Seidleck
*Assistant Examiner*—Gregory Listvoyb
(74) *Attorney, Agent, or Firm*—Schwegman, Lundberg & Woessner, P.A.

(57) ABSTRACT

The invention relates to amide-containing polymers of the general formula (I)

$$A-X-CO-(CH_2)_2-NR^1-R^2-[Y-R^3-Y-R^4]_a-B \qquad (I)$$

and also their salts with carboxylic acids, phosphoric esters and sulphonic acids. The invention further relates to processes for preparing the amide-containing polymers and to their use as rheology control agents.

7 Claims, No Drawings

AMIDE-CONTAINING POLYMERS FOR RHEOLOGY CONTROL

This application claims priority under U.S.C. 119 to German Application No. 10 2005 049 301.7 filed Oct. 12, 2005, which application is incorporated herein by reference and made a part hereof.

The invention relates to amide-containing polymers for the control of rheology in liquid polymer systems such as, for example, solvent-borne, solvent-free and aqueous coating materials, PVC plastisols, epoxide-based coatings and unsaturated polyester resins.

To control the rheology of liquid systems it is common to use silicas, hydrogenated castor oil or organically modified bentonites, as described for example in U.S. Pat. Nos. 4,208,218, 4,410,364 and 4,412,018. Polyamide waxes as well are widely employed. Within the field of polyamides and polyamide esters there exist numerous patents, such as DE 69523221, EP 0528363, EP 0239419, U.S. Pat. Nos. 5,510,452 and 5,349,011 for example. Use is also made, however, of combinations of modified bentonites with polyamides, as described in EP 0509202 and DE 69704691.

Disadvantageous features of these materials include the fact that they are usually dry solids or pastes, which have to be converted to a semi-finished product by means of solvents and application of shearing forces, and/or introduced into liquid coating systems, for example, by means of specific temperature control. Unless the necessary temperatures are observed, the finished coating system will contain crystallites, which lead to defects in the coating. The general disadvantage of these materials is that they result in turbidity and haze in clear, transparent coatings.

Moreover, the handling of dry products, which give rise to dusts in processing, is undesirable.

The polyamide esters, although they are frequently liquid, are nevertheless significantly less effective than the inherently solid materials.

Other solutions to rheology control have been set out in EP 0 198 519. There an isocyanate is reacted with an amine in the presence of binders to form a urea which forms acicular crystals in a very finely disperse form. These modified binders are offered as rheology-controlling and sag-preventing binders, and are termed sag control agents.

The disadvantage of these products is that they are always attached to the binders in which they have been produced, and, consequently, the subsequent universal correction of existing systems is not a possibility.

EP 0 006 252 describes a process for preparing a thixotropic agent that removes some of the disadvantages referred to above, by providing urea urethanes which are prepared in aprotic solvents in the presence of LiCl by reaction of isocyanate adducts with polyamines. The disadvantage of the products thus prepared lies in the undefined structure of the urea urethanes, which is caused by the preparation process. In the course of the said process, diisocyanates and monoalcohols are employed in equal molar amounts. This produces not only NCO-functional monoadducts but also non-NCO-functional diadducts. Moreover, a certain fraction of monomeric diisocyanate remains unreacted. The proportions of the various products fluctuate, depending on the accessibility of the NCO group and the reaction regime employed, such as temperature and time. All of the adducts prepared in this way, however, include relatively large amounts of unreacted diisocyanate, leading, on further reaction of polyamines, to uncontrolled chain extension of the molecule. These products then show a propensity toward precipitation phenomena or premature gelling and, accordingly, to the formation of so-called "seeds" in the binder. U.S. Pat. No. 6,420,466 gets round these disadvantages by removing the excess isocyanate. The products described in that patent, however, have the disadvantage that they yield stable solutions only in solvents of high polarity, such as N-methylpyrrolidone (NMP), for example, with the assistance of alkali metal salts.

It is an object of the present invention, therefore, to provide products suitable for rheology control in liquid polymer systems, which comprise polymers having a more defined structure and so ensuring a better profile of action and improved reproducibility of the rheology control, and which, in particular, avoid the disadvantages, outlined above, of the prior-art additives.

Surprisingly it has been found that these objects are achieved by provision of amide-containing polymers of the general formula (I)

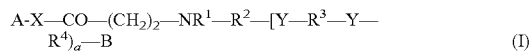

and also their salts with carboxylic acids, phosphoric esters and sulphonic acids, where A is $R^5$ or $R^6$—Y—$[R^4$—Y—$R^3$—Y$]_b$—$R^2$—$NR^1$—$(CH_2)_2$—CO—X—$R^7$ and B is Y—$R^6$ or $NR^1$—$(CH_2)_2$—CO—X—$R^5$, and where $R^1$ is H, $(CH_2)_2$—CO—X—$R^5$ and/or CONH—R' with R'=$R^8$ or —$C_6H_3(CH_3)$—NHCOO—$R^8$, $R^2$, $R^3$, $R^4$ and $R^7$ independently of one another are a ($C_1$-$C_{40}$)alkylene, ($C_3$-$C_{40}$) alkenylene, ($C_5$-$C_{40}$)cyclo-alkylene, arylene, ($C_7$-$C_{40}$)aralkylene or polyoxyalkylene radical or a polyester radical, $R^5$ is H, a ($C_1$-$C_{22}$)alkyl, aryl, ($C_7$-$C_{12}$)aralkyl, ($C_5$-$C_{12}$)-cycloalkyl, hydroxyalkyl or N,N'-dialkylamino radical, a hydroxyl, ($C_1$-$C_{22}$) alkoxy, ($C_5$-$C_{12}$) cycloalkoxy, or ($C_7$-$C_{12}$)aralkoxypolyoxyalkylene radical, or a ($C_1$-$C_{22}$)-alkanol-, ($C_5$-$C_{12}$) cycloalkanol-, ($C_7$-$C_{12}$) aralkanol-started or a ($C_1$-$C_{22}$)alkoxy-, ($C_5$-$C_{12}$)cycloalkoxy-, or ($C_7$-$C_{12}$) aralkoxypolyoxyalkylene-started polyester, $R^6$ is a ($C_1$-$C_{30}$)alkyl, ($C_3$-$C_{22}$)alkenyl, hydroxyalkyl, ($C_4$-$C_{13}$)cycloalkyl, aryl or ($C_7$-$C_{12}$)aralkyl radical, $R^8$ is a ($C_1$-$C_{22}$)alkyl, aryl, ($C_7$-$C_{12}$)aralkyl, or ($C_5$-$C_{12}$)-cycloalkyl radical, a ($C_1$-$C_{22}$)alkoxy, ($C_5$-$C_{12}$)cyclo-alkoxy, or ($C_7$-$C_{12}$)aralkoxypolyoxyalkylene radical, a ($C_1$-$C_{22}$) alkanol-, ($C_5$-$C_{12}$)cycloalkanol-, or ($C_7$-$C_{12}$)aralkanol-started or a ($C_1$-$C_{22}$)alkoxy-, ($C_6$-$C_{12}$)cycloalkoxy-, or ($C_7$-$C_{12}$)aralkoxypolyoxyalkylene-started polyester, X is identical or different radicals O, NH or $NR^9$, $R^9$ is a ($C_1$-$C_{22}$)alkyl, aryl, ($C_7$-$C_{12}$)aralkyl, hydroxy-alkyl, ($C_5$-$C_{12}$)cycloalkyl radical, Y is one or more of the following groups COO, OCO, NHCO, CONH, NHCOO, OOCNH, NHCONH, and a and b independently of one another are a number from 1 to 19.

The definitions of the radicals A, B, $R^1$, $R^2$, $R^3$, $R^4$, $R^5$, $R^6$, $R^7$, $R^8$, $R^9$, R', X and Y and also of the indices a and b correspond to the above definitions in the context of this invention, irrespective of the compounds in which they feature. Preferred versions of these radicals are found in the respective subsections.

Where one or more of the radicals $R^2$, $R^3$, $R^4$, $R^5$, $R^7$ and/or $R^8$ contain a polyoxyalkylene fraction, these radicals, irrespective of the compounds in which they feature, are constructed preferably from ethylene oxide, propylene oxide and/or butylene oxide units, in random or blockwise arrangement, and, where appropriate, one or more of these units are substituted by styrene units. Particular preference is given to ethylene oxide radicals and propylene oxide radicals.

Where one or more of the radicals $R^2$, $R^3$, $R^4$, $R^5$, $R^7$ and/or $R^8$ comprise a polyester radical, these radicals, irrespective of the compounds in which they feature, are constructed preferably on the basis of one or more ($C_1$-$C_{18}$)hydroxycarboxylic acids or one or more lactones, such as β-propiolactone, δ-valerolactone, ε-caprolactone and ($C_1$-$C_6$)alkyl-substituted ε-caprolactone.

The radicals $R^1$ are H, $(CH_2)_2$—CO—X—$R^5$ and/or CONH—R' with R'=$R^8$ or —$C_6H_3(CH_3)$—NHCOO—$R^8$, such as, for example, CONH—$C_{18}H_{37}$ and/or CONH—$C_6H_3$ $(CH_3)$—NHCOO$C_4H_9$.

The radicals $R^2$ and $R^4$ independently of one another are preferably a ($C_2$-$C_{18}$)alkylene, ($C_7$-$C_{15}$)aralkylene radical, more preferably a ($C_2$-$C_{12}$)alkylene, ($C_7$-$C_{12}$)-aralkylene radical, very preferably a ($C_2$-$C_8$)alkylene, ($C_7$-$C_9$)aralkylene radical, such as, for example, a hexa-methylene, octamethylene or m-xylylene radical. Preferably the radicals $R^2$ and $R^4$ are identical.

$R^3$ is a ($C_2$-$C_{40}$)alkylene, ($C_3$-$C_{40}$)alkenylene, ($C_5$-$C_{40}$)-cycloalkylene, arylene or ($C_7$-$C_{40}$)aralkylene radical, preferably a ($C_{30}$-$C_{40}$)alkylene, ($C_{30}$-$C_{40}$)alkenylene, ($C_{30}$-$C_{40}$) cycloalkylene, arylene or ($C_{30}$-$C_{40}$)aralkylene radical, such as, for example, the radical between the two carboxylic acid groups of dimer acid. With particular preference $R^3$ is a $C_{34}$ radical.

$R^5$ is preferably a ($C_1$-$C_{22}$)alkyl, a hydroxyl or an alkoxypolyoxyalkylene radical.

$R^6$ is preferably a ($C_1$-$C_{30}$)alkyl or a ($C_3$-$C_{22}$)alkenyl radical, more preferably a ($C_{12}$-$C_{30}$)alkyl or a ($C_{12}$-$C_{22}$)-alkenyl radical and with very particular preference a ($C_{12}$-$C_{20}$) alkyl or a ($C_{12}$-$C_{20}$)alkenyl radical, such as, for example, a $C_{17}$-alkyl or a $C_{17}$-alkenyl radical.

$R^7$ is preferably a ($C_1$-$C_{18}$)alkylene or a polyoxyalkylene radical, and $R^8$ is a ($C_1$-$C_{22}$)alkyl radical. X is preferably identical or different radicals O or NH, and Y is preferably one or more of the groups NHCO and CONH.

The indices a and b are independently of one another a number from 1 to 19, more preferably from 2 to 7, and are preferably identical.

Particularly preferred embodiments of the invention relate to compounds of the general formula (I) with A=$R^5$ and B=$NR^1$—$(CH_2)_2$—CO—X—$R^5$, giving the general formula (II):

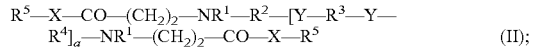

compounds of the general formula (I) with A=$R^5$ and B=Y—$R^6$, giving the general formula (III)

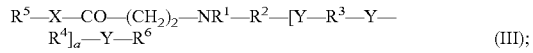

and compounds of the general formula (I) with A=$R^6$—Y—$[R^4$—Y—$R^3$—Y$]_a$—$R^2$—$NR^1$—$(CH_2)_2$—CO—X—$R^7$ and B=Y—$R^6$, giving the general formula (IV):

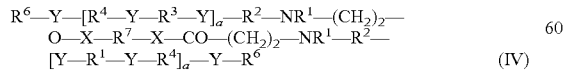

Besides the amide-containing polymers, the present invention also provides a process for preparing amide-containing polymers of the general formula (I)

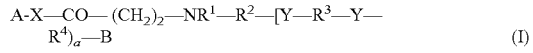

also their salts with carboxylic acids, phosphoric esters and sulphonic acids, where A is $R^1$ or $R^6$—Y—$[R^4$—Y—$R^3$—Y$]_b$—$R^2$—$NR^1$—$(CH_2)_2$—CO—X—$R^7$ and B is Y—$R^6$ or $NR^1$—$(CH_2)_2$—CO—X—$R^5$, and where $R^1$ is H, $(CH_2)_2$—CO—X—$R^5$ and/or CONH—R' with R'=$R^8$ or —$C_6H_3$ $(CH_3)$—NHCOO—$R^8$, $R^2$, $R^3$, $R^4$ and $R^7$ independently of one another are a ($C_1$-$C_{40}$)alkylene, ($C_3$-$C_{40}$)alkenylene, ($C_5$-$C_{40}$)cyclo-alkylene, arylene, ($C_7$-$C_{40}$)aralkylene or polyoxyalkylene radical or a polyester radical, $R^5$ is H, a ($C_1$-$C_{22}$)alkyl, aryl, ($C_7$-$C_{12}$)aralkyl, ($C_5$-$C_{12}$)-cycloalkyl, hydroxyalkyl or N,N'-dialkylamino radical, a hydroxyl, ($C_1$-$C_{22}$)alkoxy, ($C_5$-$C_{12}$)cycloalkoxy, or ($C_7$-$C_{12}$)aralkoxypolyoxyalkylene radical, or a ($C_1$-$C_{22}$)-alkanol-, ($C_5$-$C_{12}$)cycloalkanol-, ($C_7$-$C_{12}$)aralkanol-started or a ($C_1$-$C_{22}$)alkoxy-, ($C_5$-$C_{12}$)cycloalkoxy-, or ($C_7$-$C_{12}$) aralkoxy-polyoxyalkylene-started polyester, $R^6$ is a ($C_1$-$C_{30}$)alkyl, ($C_3$-$C_{22}$)alkenyl, hydroxyalkyl, ($C_4$-$C_{13}$)cycloalkyl, aryl or ($C_7$-$C_{12}$)aralkyl radical, $R^8$ is a ($C_1$-$C_{22}$)alkyl, aryl, ($C_7$-$C_{12}$)aralkyl, or ($C_5$-$C_{12}$)-cycloalkyl radical, a ($C_1$-$C_{22}$)alkoxy, ($C_5$-$C_{12}$)cyclo-alkoxy, or ($C_7$-$C_{12}$)aralkoxy-polyoxyalkylene radical, a ($C_1$-$C_{22}$) alkanol-, ($C_5$-$C_{12}$)cycloalkanol-, or ($C_7$-$C_{12}$)-aralkanol-started or a ($C_1$-$C_{22}$)alkoxy-, ($C_6$-$C_{12}$)cyclo-alkoxy-, or ($C_7$-$C_{12}$)aralkoxypolyoxyalkylene-started polyester, X is identical or different radicals O, NH or $NR^9$, $R^9$ is a ($C_1$-$C_{22}$)alkyl, aryl, ($C_7$-$C_{12}$)aralkyl, hydroxy-alkyl, ($C_5$-$C_{12}$) cycloalkyl radical, Y is one or more of the following groups COO, OCO, NHCO, CONH, NHCOO, OOCNH, NHCONH, and a and b independently of one another are a number from 1 to 19, wherein (A) one or more compounds of the general formulae (V) and (VIII)

$$H_2N—R^2—[Y—R^3—Y—R^4]_a—NH_2 \qquad (V)$$

$$H_2N—R^2—[Y—R^3—Y—R^4]_a—YR^6 \qquad (VIII)$$

are reacted with one or more compounds of the general formulae (VI) and (IX)

$$R^5—X—CO—CH=CH_2 \qquad (VI)$$

$$H_2C=HC—CO—X—R^7—X—CO—CH=CH_2 \qquad (IX)$$

to form compounds with $R^1$=hydrogen, using 0.8 to 1.2 mol of CH=$CH_2$ groups in the compounds of the formulae (VI) and (IX) per mole of $NH_2$ groups in the compounds of the general formulae (V) and (VIII), and (B) if $R^1$ in whole or in part is $(CH_2)_2$—CO—X—$R^5$ and/or CONH—R', the compounds from step (A) are reacted with one or more compounds of the general formulae (VI) and (VII)

$$R^5—X—CO—CH=CH_2 \qquad (VI)$$

$$R'—NCO \qquad (VII)$$

using up to 1.2 mol of compounds of the general formula (VI) and/or (VII) per mole of $NR^1$ groups in the compounds from step (A), and (C) where the compounds of the general formula (I) are salts of carboxylic acids, phosphoric esters and sulphonic acids, a reaction of the compounds from step (A) or (B) with carboxylic acids, phosphoric esters and sulphonic acids takes place.

In one preferred embodiment (A) one or more compounds of the general formula (V)

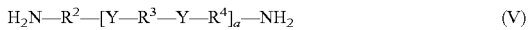

are reacted with one or more compounds of the general formula (VI)

to form compounds with $R^1$=hydrogen, using 0.8 to 1.2 mol of CH=$CH_2$ groups in the compounds of the formula (VI) per mole of $NH_2$ groups in the compounds of the general formula (V), and (B) if $R^1$ in whole or in part is $(CH_2)_2$—CO—X—$R^5$ and/or CONH—R', the compounds from step (A) are reacted with one or more compounds of the general formulae (VI) and (VII)

using up to 1.2 mol of compounds of the general formula (VI) and/or (VII) per mole of $NR^1$ groups in the compounds from step (A), and (C) where the compounds of the general formula (I) are salts of carboxylic acids, phosphoric esters and sulphonic acids, a reaction of the compounds from step (A) or (B) with carboxylic acids, phosphoric esters and sulphonic acids takes place.

In another preferred embodiment (A) one or more compounds of the general formula (VIII)

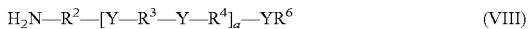

are reacted with one or more compounds of the general formula (VI)

to form compounds with $R^1$=hydrogen, using 0.8 to 1.2 mol of CH=$CH_2$ groups in the compounds of the formula (VI) per mole of $NH_2$ groups in the compounds of the general formula (VIII), and (B) if $R^1$ in whole or in part is $(CH_2)_2$—CO—X—$R^5$ and/or CONH—R', the compounds from step (A) are reacted with one or more compounds of the general formulae (VI) and (VII)

using up to 1.2 mol of compounds of the general formula (VI) and/or (VII) per mole of $NR^1$ groups in the compounds from step (A), and (C) where the compounds of the general formula (I) are salts of carboxylic acids, phosphoric esters and sulphonic acids, a reaction of the compounds from step (A) or (B) with carboxylic acids, phosphoric esters and sulphonic acids takes place.

In a further preferred embodiment (A) one or more compounds of the general formula (VIII)

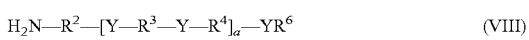

are reacted with one or more compounds of the general formula (IX)

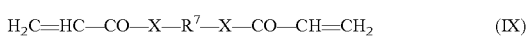

to form compounds with $R^1$=hydrogen, using 0.8 to 1.2 mol of CH=$CH_2$ groups in the compounds of the formula (IX) per mole of $NH_2$ groups in the compounds of the general formula (VIII), and (B) if $R^1$ in whole or in part is $(CH_2)_2$—CO—X—$R^5$ and/or CONH—R', the compounds from step (A) are reacted with one or more compounds of the general formulae (VI) and (VII)

using up to 1.2 mol of compounds of the general formula (VI) and/or (VII) per mole of $NR^1$ groups in the compounds from step (A), and (C) where the compounds of the general formula (I) are salts of carboxylic acids, phosphoric esters and sulphonic acids, a reaction of the compounds from step (A) or (B) with carboxylic acids, phosphoric esters and sulphonic acids takes place.

In the aforementioned preferred embodiments of the process of the invention, the amount of the compounds of the general formula (VI) that is specified in step (B) can be used in step (A), instead of step (B), in addition to the amount of the compounds of the general formula (VI) that is specified in step (A).

The reaction in step (A) is carried out preferably at a temperature of 60 to 100° C., more preferably at a temperature of 70 to 90° C.

The reaction in step (B), in the case of reaction with compounds of the general formula (VII), is carried out preferably at a temperature of 50 to 100° C., more preferably 60 to 80° C., and, in the case of reaction with a compound of the general formula (VI), is carried out at a temperature of preferably 60 to 100° C., more preferably 70 to 90° C.

In the text below, the process of the invention is elucidated using specific examples.

Compounds of the formula (II) with $R^1$=—H, —$(CH_2)_2$—CO—X—$R^5$, —CONH—R' with R'=$R^8$ or —$C_6H_3(CH_3)$—NHCOO—$R^8$ can be prepared, for example, by reacting one or more compounds of the general formula (V):

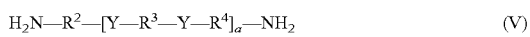

where $R^2$, $R^3$ and $R^4$ independently of one another are a $(C_2-C_{40})$ alkylene, $(C_3-C_{40})$ alkenylene, $(C_5-C_{40})$ cyclo-alkylene, arylene, $(C_7-C_{40})$aralkylene or polyoxyalkylene radical, Y is one or more of the following groups Coo, OCO, NHCO, CONH, NHCOO, OOCNH, NHCONH, and a is a number from 1 to 19, with one or more compounds of the general formula (VI):

where $R^5$ is H, a $(C_1-C_{22})$alkyl, aryl, $(C_7-C_{12})$aralkyl, $(C_5-C_{12})$cycloalkyl, hydroxyalkyl, or N,N'-dialkylamino radical, a hydroxyl, $(C_1-C_{22})$alkoxy, $(C_5-C_{12})$cycloalkoxy, or $(C_7-C_{12})$aralkoxypolyoxyalkylene radical, the oxy-alkylene radical being ethylene oxide, propylene oxide or butylene oxide, including mixtures thereof, and it being possible for parts of the oxyalkylene radical to be substituted by styrene oxide, or is a $(C_1-C_{22})$-alkanol-, $(C_5-C_{12})$cycloalkanol-, $(C_7-C_{12})$aralkanol-started or a $(C_1-C_{22})$alkoxy-, $(C_5-C_{12})$cycloalkoxy-, or $(C_7-C_{12})$aralkoxypolyoxyalkylene-started polyester based, for example, on $(C_1-C_{18})$hydroxycarboxylic acids or on lactones such as β-propiolactone, δ-valerolactone, ε-caprolactone or (C₁-C₆)alkyl-substituted ε-caprolactone, including mixtures thereof, for example, X is O, NH or NR⁹, and R⁹ is (C₁-C₂₂)alkyl, aryl, (C₇-C₁₂)aralkyl, hydroxyalkyl, (C₅-C₁₂) cycloalkyl radical and subsequently reacting the product, where appropriate, with compounds of the general formula (VII):

R'—NCO (VII)

where R' is R⁸ or —C₆H₃(CH₃)—NHCOO—R⁸ and R⁸ is a (C₁-C₂₂)alkyl, aryl, (C₇-C₁₂)aralkyl, or (C₅-C₁₂)-cycloalkyl radical, a (C₁-C₂₂)alkoxy, (C₅-C₁₂)cyclo-alkoxy, or (C₇-C₁₂)aralkoxypolyoxyalkylene radical, the oxyalkylene radical being ethylene oxide, propylene oxide or butylene oxide, including mixtures thereof, and parts of the oxyalkylene radical being substituted, where appropriate, by styrene oxide, is a (C₁-C₂₂)-alkanol-, (C₅-C₁₂) cycloalkanol-, or (C₇-C₁₂) aralkanol-started or a (C₁-C₂₂)alkoxy-, (C₆-C₁₂)cycloalkoxy-, or (C₇-C₁₂)aralkoxypolyoxyalkylene-started polyester based, for example, on (C₁-C₁₈)hydroxycarboxylic acids or on lactones such as β-propiolactone, δ-valerolactone, ε-caprolactone or (C₁-C₆)alkyl-substituted ε-caprolactone, including mixtures thereof, for example.

The intermediates (V) of the invention are obtainable, for example, by reacting polycarboxylic acids, preferably dicarboxylic acids, and/or dicarboxylic anhydrides, with diamines, the ratio of diamine to polycarboxylic acid being 2:1 to 20:19, more preferably 3:2 to 8:7.

The diamines are preferably aliphatic and araliphatic primary diamines, such as ethylenediamine, neopentanediamine, 1,2- and 1,3-propanediamine, 1,4-butanediamine, 1,5-pentanediamine, 1,6-hexa-methylenediamine (also as a solution in water), 1,8-octamethylenediamine, 1,12-dodecamethylenediamine, cyclohexyldiamine, 4,4'-diaminodicyclohexylmethane, 3,3'-dimethyl-4,4'-diaminodicyclohexylmethane, isophoronediamine, 4,7-dioxadecane-1,10-diamine, 4,11-dioxatetradecane-1,14-diamine, 4,7,10-trioxadecane-1,13-diamine, polyoxyalkylenediamines which contain ethylene oxide and/or propylene oxide groups, arranged randomly or blockwise, possess a number-average molecular weight of 148 to 4000 g/mol and are obtainable for example as Jeffamine® D and Jeffamine® ED from Huntsman, polytetrahydrofurandiamines, and also para- and meta-xylylenediamine. Preference is given to using 1,6-hexamethylenediamine, 1,8-octamethylenediamine and meta-xylylenediamine. It is likewise possible to use amines of the type H₂N—R—NR—R—NH₂, R independently being (C₁-C₁₈)alkyl or (C₁-C₄)alkoxy. One example of such is N,N'-bis (3-aminopropyl)methylamine. Alternatively it is possible to use dihydrazides such as, for example, oxalic dihydrazide, succinic dihydrazide or adipic dihydrazide. The use of mixtures of the diamines, including mixtures with the dihydrazides as well, is likewise possible. The diamines can also be used as carbonate compounds, which in the condensation reaction react with the polycarboxylic acids with elimination of water and of CO₂ to form the amide moieties preferred in accordance with the invention.

The polycarboxylic acids are preferably aliphatic, cycloaliphatic or aromatic, linear or branched, saturated or unsaturated dicarboxylic acids having at least 2, more preferably 3 to 40, C atoms. Examples of such polycarboxylic acids are adipic acid, oxalic acid, malonic acid, succinic acid, glutaric acid, pimelic acid, suberic acid, sebacic acid, azelaic acid, undecanedioic acid, 1,11-undecanedicarboxylic acid, dodecanedioic acid, hexacanedioic acid, docosanedioic acid, maleic acid, fumaric acid, terephthalic acid or isophthalic acid, used alone or in mixtures. Acid anhydrides such as maleic anhydride, glutaric anhydride, phthalic anhydride and succinic anhydride, which where appropriate are modified with alkyl or alkylene groups, such as dodecenylsuccinic anhydride, for example, are likewise included in the invention. Polymeric polycarboxylic acids such as the dicarboxylic acid of polybutadiene, for example, can also be used, as can hydroxy-functional polycarboxylic acids such as tartaric acid, citric acid and hydroxyphthalic acid, for example. Oxydicarboxylic acids such as 3,6,9-trioxyundecanedioic acid and polyglycoldioic acid are likewise included. Dimerized fatty acids, known to the skilled person as dimer acids, having a carbon length of 36 C atoms, are especially preferred. These dimer acids may contain not only a low monomer content (typically <8 percent by weight) but also a fraction of not more than 25 percent by weight of trimer acid.

The polycarboxylic acids can be replaced partly by diisocyanates and the diamines partly by diols, in which case there may be ester, urethane and/or urea groups alongside the preferred amide moieties in the compounds of the general formula (V).

The diols, alone or in mixtures, are preferably polyoxyalkylene diols, polyoxyalkenyl diols, which where appropriate are modified with (C₁-C₄)alkyl and/or alkoxy groups, polyester diols, mixed polyesterpolyoxy-alkylene diols, polylactone diols, mixed polyoxyalkylenepolylactone diols, polycarbonate diols, polyolefin diols, polyacrylate diols, alkoxylated bisphenol A diols, diols of the α,ω-dihydroxyalkylenesiloxane type, and alkoxylated compounds thereof having an average molecular weight Mₙ of 250 to 5000 g/mol.

As diisocyanates it is possible with preference to use aliphatic, cycloaliphatic and aromatic diisocyanates or mixtures thereof. Examples of such diisocyanates are tetramethylene 1,4-diisocyanate, hexamethylene 1,6-diisocyanate, 2,2,4-trimethylhexamethylene 1,6-diisocyanate, decamethylene 1,10-diisocyanate, cyclohexylene 1,4-diisocyanate, phenylene p-diisocyanate, phenylene m-diisocyanate, tolylene 2,6-diisocyanate, tolylene 2,4-diisocyanate and mixtures thereof, xylylene p- and m-diisocyanate, naphthylene 1,5-diisocyanate, isophorone diisocyanate, 4,4'-diisocyanatodicyclohexylmethane, 3,3'-dimethyl-4,4'-bisphenylene diisocyanate, 3,3'-dimethyldiisocyanatodiphenylmethane, the isomer mixtures of 2,4'- and 4,4'-diisocyanatodiphenylmethane, and C₃₆ dimer diisocyanate.

Compounds of the general formula (V) are prepared under conditions of the kind known to the skilled person. The reaction temperature for the condensation reaction of the dicarboxylic acids with diamines or diols is preferably 100 to 250° C., more preferably 140 to 200° C. The ratio of diamine and polycarboxylic acid is chosen such that for n equivalents of polycarboxylic acid (n+1) equivalents of diamine are used, so that the condensation product has an amine number of preferably 5 to 180 and more preferably of 15 to 100, based on 100% active substance.

Compounds of the general formula (VI) that are used are preferably, if X is O, acrylic acid and also its salts, such as sodium acrylate, potassium acrylate or ammonium acrylate, for example, and acrylic acid alkyl esters of linear, branched or cycloaliphatic alcohols having 1 to 22 C atoms, such as, for example, methyl acrylate, ethyl acrylate, n-propyl acrylate, isopropyl acrylate, n-butyl acrylate, isobutyl acrylate, tert-butyl acrylate, pentyl acrylate, hexyl acrylate, 2-ethylhexyl acrylate, n-octyl acrylate, isooctyl acrylate, 3,5,5-trimethylhexyl acrylate, octyldecyl acrylate, isodecyl acrylate, lauryl acrylate, tridecyl acrylate, C16/C18 alkyl acrylate, stearyl acrylate, behenyl acrylate, cyclohexyl acrylate, tetrahydrofurfuryl acrylate, 2-norbornyl acrylate, isobornyl acrylate, dicyclopentadienyl acrylate, dihydrodicyclopentadienyl acrylate and benzyl acrylate. Likewise included are acrylic acid aryl esters such as, for example, phenyl acrylate or 2-phenoxyethyl acrylate. The use of acrylic acid hydroxyalkyl esters of linear, branched or cycloaliphatic diols having 2 to 36 C atoms, such as 2-hydroxyethyl acrylate, 3-hydroxypropyl acrylate or 4-hydroxybutyl acrylate, for example, is likewise possible, as is the use of caprolactone- and/or valerolactone-modified hydroxyalkyl acrylates having an average molecular weight $M_n$ of 220 to 1200, the hydroxy acrylates being derived preferably from linear, branched or cycloaliphatic diols having 2 to 8 C atoms. Polyoxyalkylene acrylates, such as polyoxyethylene acrylates, polyoxypropylene acrylates or polyoxybutylene acrylates, mixed polyoxyethylene-polyoxypropylene acrylates or mixtures of polyoxy-ethylene acrylates and polyoxypropylene acrylates with higher-homologous oxyalkylene acrylates or with styrene oxide, having 5 to 100 C atoms, find use not only as OH-functional compounds but also as compounds capped by alkyl, allyl or aralkyl with 1 to 22 C atoms, such as, for example, methoxy-, ethoxy-, lauroxy- or stearoxy-polyoxyethylene acrylate, octoxy-, stearoxy- or allyl-oxypolyoxyethylene-polyoxypropylene acrylate or nonyl-phenoxypolyoxyalkylene acrylate. Aminoalkyl acrylates such as N,N-dimethylaminoethyl acrylate or N,N'-dimethylaminopropyl acrylate, for example, may likewise be used.

Where X in the compounds of the general formula (VI) is NH, it is possible, as well as acrylamide, to use substituted acrylamides as well, such as tert-butyl acrylamide, isopropylacrylamide, N-methylolacrylamide, N-butoxymethylacrylamide, N-isobutoxymethylacrylamide, N,N'-dimethylaminopropylacrylamide, phenylacrylamide and 2-acrylamido-2-methyl-1-propanesulphonic acid (AMPS), and its salts. If X is NR, then, for example, N,N'-dimethylacrylamide is employed. Mixtures of the individual acrylic esters with one another and together with the acrylamides are likewise in accordance with the invention.

Suitable compounds of the general formula (VII) include preferably the following monoisocyanates: methyl isocyanate, ethyl isocyanate, propyl isocyanate, n-butyl isocyanate, tert-butyl isocyanate, isobutyl isocyanate, pentyl isocyanate, neopentyl isocyanate, 2-ethylhexyl isocyanate, octyl isocyanate, cyclohexyl isocyanate, phenyl isocyanate, tolyl isocyanate, 1-naphthyl isocyanate, 2-naphthyl isocyanate, stearyl isocyanate and also the isocyanate-containing monoadducts known from U.S. Pat. No. 6,420,466 of the general formula OCN—$C_6H_3(CH_3)$—NHCOO—$R^8$, where $R^8$ is preferably a ($C_1$-$C_{22}$)alkyl, aryl, ($C_7$-$C_{12}$)aralkyl, or ($C_5$-$C_{12}$)cycloalkyl radical, a ($C_1$-$C_{22}$)alkoxy, ($C_5$-$C_{12}$) cycloalkoxy or ($C_7$-$C_{12}$) aralkoxypolyoxyalkylene radical, the oxyalkylene radical being ethylene oxide, propylene oxide or butylene oxide, including mixtures thereof, and it being possible for parts of the oxyalkylene radical to be substituted by styrene oxide, or is a ($C_1$-$C_{22}$)alkanol-, ($C_5$-$C_{12}$)cycloalkanol-, ($C_7$-$C_{12}$)aralkanol-started or a ($C_1$-$C_{22}$)alkoxy-, ($C_5$-$C_{12}$) cycloalkoxy-, or ($C_7$-$C_{12}$) aralkoxypolyoxyalkylene-started polyester based, for example, on ($C_1$-$C_{18}$)hydroxycarboxylic acids or on lactones such as, for example, β-propiolactone, δ-valerolactone, ε-caprolactone or ($C_1$-$C_6$)alkyl-substituted ε-caprolactone, including mixtures thereof. The individual monoisocyanates can also be used in mixtures.

The addition reaction between the compounds of the general formula (V) and (VI) is carried out preferably at a reaction temperature of 60 to 100° C., more preferably of 70 to 90° C. The ratio between (V) and (VI) is chosen such that per mole of compound (V), if $R^1$ in compound (II) is H, use is made of preferably 1.8 mol to 2.2 mol, more preferably 1.9 mol to 2.1 mol and very preferably 2 mol of the compound of the general formula (VI) and, where $R^1$ in compound (II) is —$(CH_2)_2$—CO—X—$R^5$, use is made of preferably 3.8 mol to 4.2 mol, more preferably 3.9 mol to 4.1 mol and very preferably 4 mol of compound (VI). Where $R^1$ in compound (II)=—$(CH_2)_2$—CO—X—$R^5$, the acrylic esters and acrylamides can be added individually or in mixtures simultaneously or successively to compound (V). The reaction can be carried out in the presence or absence of solvents. Suitable solvents are all aliphatic, aromatic, protic and aprotic solvents, such as methoxypropyl acetate, cyclohexane, toluene, xylene, higher-boiling alkyl-benzenes or isoparaffins, N-methylpyrrolidone or N-ethylpyrrolidone, and also alcohols such as ethanol, propanol, isobutanol or glycols such as butyl glycol, for example. Mixtures of solvents can also be used.

Where $R^1$ in the compound of the general formula (II) is CONH—R', with R' being $R^8$ or $C_6H_3(CH_3)$—NHCOO—$R^8$, preferably 1.8 mol to 2.2 mol, more preferably 1.9 mol to 2.1 mol, very preferably 2 mol of the compound of the general formula (VII) is added to 1 mol of the adduct of compound (V) and (VI), at a reaction temperature of 50 to 100° C., more preferably of 60 to 80° C. The monoisocyanates may be the same or different. This reaction can be carried out with or without catalyst. Suitable catalysts include not only organotin compounds such as dibutyltin dilaurate (DBTL), for example, but also tertiary amines such as diazabicyclo-[2.2.2] octane (DABCO), for example. The reaction can be carried out with or without solvent. Suitable solvents are all aliphatic, aromatic, and aprotic solvents, such as methoxypropyl acetate, cyclohexane, toluene, xylene, higher-boiling alkyl-benzenes or isoparaffins, N-methyl-pyrrolidone or N-ethylpyrrolidone, for example. Mixtures of solvents can also be used.

Compounds of the general formula (III)

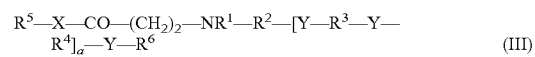

$$R^5-X-CO-(CH_2)_2-NR^1-R^2-[Y-R^3-Y-R^4]_a-Y-R^6 \quad (III)$$

in which $R^1$ is H, $(CH_2)_2$—CO—X—$R^5$ or CONH—R' and R' is $R^8$ or $C_6H_3$ ($CH_3$)—NHCOO—$R^8$ can be prepared, for example, by reacting one or more compounds of the general formula (VIII):

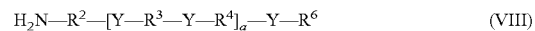

$$H_2N-R^2-[Y-R^3-Y-R^4]_a-Y-R^6 \quad (VIII)$$

where $R^2$, $R^3$ and $R^4$ independently of one another are a ($C_2$-$C_{40}$)alkylene, ($C_3$-$C_{40}$)alkenylene, ($C_5$-$C_{40}$)cyclo-alkylene, arylene, ($C_7$-$C_{40}$)aralkylene or polyoxyalkylene radical, the oxyalkylene radical being ethylene oxide, propylene oxide or butylene oxide, including mixtures thereof, and it being possible for parts of the oxyalkylene radical to be substituted by styrene oxide, or are a polyester radical based on, for example, ($C_1$-$C_{18}$)hydroxycarboxylic acids or lactones such as β-propiolactone, δ-valerolactone, ε-caprolactone or ($C_1$-$C_6$)alkyl-substituted ε-caprolactone, including mixtures thereof, for example, Y is one or more of the following groups COO, OCO, NHCO, CONH, NHCOO, OOCNH, NHCONH, and a is a number from 1 to 19, and $R^6$ is a ($C_1$-$C_{30}$)alkyl, ($C_3$-$C_{22}$)alkenyl, hydroxyalkyl, ($C_4$-$C_{13}$)cycloalkyl, aryl or ($C_7$-$C_{12}$)aralkyl radical, with one or more compounds of the general formula (VI):

$$R^5-X-CO-CH=CH_2 \quad (VI)$$

where $R^5$ is H, a ($C_1$-$C_{22}$)alkyl, aryl, ($C_7$-$C_{12}$)aralkyl, ($C_5$-$C_{12}$)cycloalkyl, hydroxyalkyl, or N,N'-dialkylamino radical, a hydroxyl, ($C_1$-$C_{22}$)alkoxy, ($C_5$-$C_{12}$)cycloalkoxy, or ($C_7$-$C_{12}$)aralkoxypolyoxyalkylene radical, the oxy-alkylene radical being ethylene oxide, propylene oxide or butylene oxide, including mixtures thereof, and it being possible for parts of the oxyalkylene radical to be substituted by styrene oxide, or is a $(C_1-C_{22})$-alkanol-, $(C_5-C_{12})$cycloalkanol-, $(C_7-C_{12})$aralkanol-started or a $(C_1-C_{22})$alkoxy-, $(C_5-C_{12})$cycloalkoxy-, or $(C_7-C_{12})$ aralkoxypolyoxyalkylene-started polyester based, for example, on $(C_1-C_{18})$hydroxycarboxylic acids or on lactones such as β-propiolactone, δ-valerolactone, ε-caprolactone or $(C_1-C_6)$alkyl-substituted ε-caprolactone, including mixtures thereof, for example, X is O, NH or $NR^9$, and $R^9$ is $(C_1-C_{22})$alkyl, aryl, $(C_7-C_{12})$aralkyl, hydroxyalkyl, $(C_5-C_{12})$ cycloalkyl radical and subsequently reacting the product, where appropriate, with compounds of the general formula (VII):

R'—NCO (VII)

where R' is $R^8$ or —$C_6H_3(CH_3)$—NHCOO—$R^8$ and $R^8$ is a $(C_1-C_{22})$alkyl, aryl, $(C_7-C_{12})$aralkyl, or $(C_5-C_{12})$-cycloalkyl radical, a $(C_1-C_{22})$alkoxy, $(C_5-C_{12})$-cycloalkoxy, or $(C_7-C_{12})$aralkoxypolyoxyalkylene radical, the oxyalkylene radical being ethylene oxide, propylene oxide or butylene oxide, including mixtures thereof, and parts of the oxyalkylene radical being substituted, where appropriate, by styrene oxide, is a $(C_1-C_{22})$alkanol-, $(C_5-C_{12})$cycloalkanol-, or $(C_7-C_{12})$-aralkanol-started or a $(C_1-C_{22})$ alkoxy-, $(C_6-C_{12})$cycloalkoxy-, or a $(C_7-C_{12})$aralkoxypolyoxyalkylene-started polyester based, for example, on $(C_1-C_{18})$hydroxy-carboxylic acids or on lactones such as β-propiolactone, δ-valerolactone, ε-caprolactone or $(C_1-C_6)$-alkyl-substituted ε-caprolactone, including mixtures thereof, for example.

The intermediates of the invention of the general formula (VIII) are prepared under conditions of the kind known to the skilled person and are obtainable, for example, by reacting a mixture of monocarboxylic and polycarboxylic acids, preferably dicarboxylic acids, and/or dicarboxylic anhydrides, with diamines, preferably at temperatures of 100 to 250° C., more preferably 140 to 200° C., with elimination of water. Compounds of the general formula (VIII) can be prepared preferentially by first reacting the dicarboxylic acid and/or the dicarboxylic anhydride with the diamine at temperatures of 100 to 250° C., more preferably 140 to 200° C., with elimination of water, to form the condensation product of the general formula (V), having an amine number of preferably 5 to 180 and more preferably of 15 to 100, based on 100% active substance, and then, at temperatures of 100 to 250° C., more preferably 140 to 200° C., reacting compound (V) with the monocarboxylic acid, with elimination of water, to give compound (VIII), this condensation product having an amine number of preferably 3 to 80 and more preferably of 8 to 50, based on 100% active substance. The ratio of diamine to polycarboxylic acid to monocarboxylic acid is 3:2:1 to 20:19:1, more preferably 3:2:1 to 8:7:1.

The monocarboxylic and/or polycarboxylic acids can be replaced in part by monoisocyanates and diisocyanates, and the diamines can be replaced in part by diols, in which case there are ester, urethane and/or urea groups alongside the preferred amide moieties in the compounds of the general formula (VIII).

The monocarboxylic acids are saturated, mono- to poly-unsaturated, linear and branched aliphatic carboxylic acids such as, for example, acetic acid, propionic acid, butyric acid, isobutyric acid, valeric acid, isovaleric acid, caproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotinic acid, melissic acid, lauroleic acid, myristoleic acid, palmitoleic acid, petroselinic acid, oleic acid, elaidic acid, vaccenic acid, erucic acid, linoleic acid, linolenic acid, arachidonic acid, clupanodonic acid, ricinenic acid, α-eleo-stearic acid, α-parinaric acid, coconut oil fatty acid, palm-kernel oil fatty acid, coconut/palm-kernel oil fatty acid, palm oil fatty acid, cotton oil fatty acid, peanut oil fatty acid, soya oil fatty acid, sunflower oil fatty acid, rapeseed oil fatty acid and tallow fatty acid. Also used are ketocarboxylic acids such as licanic acid, for example, and aromatic monocarboxylic acids such as benzoic acid, for example. Representatives of the hydroxycarboxylic acids that may be mentioned include, for example, glycolic acid, 5-hydroxyvaleric acid, 6-hydroxycaproic acid, ricinoleic fatty acid, 12-hydroxystearic acid, 12-hydroxydodecanoic acid, 5-hydroxydodecanoic acid, 5-hydroxydecanoic acid or 4-hydroxydecanoic acid. Mixtures of the monocarboxylic acids can also be used. The addition reaction between the compounds of the general formulae (VIII) and (VI) is carried out preferably at a reaction temperature of 60 to 100° C., more preferably of 70 to 90° C. The ratio between the compounds of the general formulae (VIII) and (VI) is preferably selected such that for each mole of compound of the general formula (VIII), if $R^1$ in the compound is H, use is made of 0.8 mol to 1.2 mol, more preferably 0.9 mol to 1.1 mol and very preferably 1 mol of compound of the general formula (VI) and, where $R^1$ in the compound of the general formula (III) is $(CH_2)_2$—CO—X—$R^5$, use is made of preferably 1.8 mol to 2.2 mol, more preferably 1.9 mol to 2.1 mol and very preferably 2 mol of compound (VI). Where $R^1$ in compound (III) is $(CH_2)_2$—CO—X—$R^5$, the acrylic esters and acrylamides can be added individually or in mixtures simultaneously or successively to the compound of the general formula (VIII). The reaction can be carried out with or without solvent. Suitable solvents are all aliphatic, aromatic, protic and aprotic solvents, such as methoxypropyl acetate, cyclohexane, toluene, xylene, higher-boiling alkylbenzenes or isoparaffins, for example. N-Methylpyrrolidone or N-ethylpyrrolidone, but also alcohols such as ethanol, propanol, isobutanol or glycols such as butyl glycol, for example, are likewise suitable. Mixtures of solvents can also be used.

Where $R^1$ in the compounds of the formula (III) is CONH—R', with R'=$R^8$ or $C_6H_3(CH_3)$—NHCOO—$R^8$, preferably 0.8 mol to 1.2 mol, more preferably 0.9 mol to 1.1 mol very preferably 1 mol of the compound of the general formula (VII) is added per mole of the adduct of the compounds of the general formulae (VIII) and (VI), preferably at a reaction temperature of preferably 50 to 100° C., more preferably 60 to 80° C. The monoisocyanates may be the same or different. The reaction can be carried out with or without catalyst. Suitable catalysts include not only organotin compounds such as DBTL, for example, but also tertiary amines such as DABCO, for example. This reaction can be carried out with or without solvent. Suitable solvents are all aliphatic, aromatic and aprotic solvents such as, for example, methoxypropyl acetate, cyclohexane, toluene, xylene, higher-boiling alkylbenzenes or isoparaffins, N-methylpyrrolidone or N-ethyl-pyrrolidone. Mixtures of solvents can also be used.

Compounds of the general formula (IV)

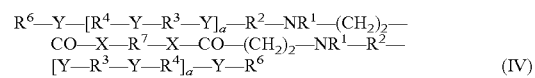

(IV)

with $R^1$=H, —$(CH_2)_2$—CO—X—$R^5$, —CONH—R' with R'=$R^8$ or —$C_6H_3$ $(CH_3)$—NHCOO—$R^8$ can be prepared, for example, by reacting one or more compounds of the general formula (VIII):

$$H_2N—R^2—[Y—R^3—Y—R^4]_a—Y—R^6 \qquad (VIII)$$

where $R^2$, $R^3$ and $R^4$ independently of one another are a $(C_2$-$C_{40})$ alkylene, $(C_3$-$C_{40})$ alkenylene, $(C_5$-$C_{40})$ cycloalkylene, arylene, $(C_7$-$C_{40})$aralkylene or polyoxyalkylene radical, the oxyalkylene radical being ethylene oxide, propylene oxide or butylene oxide, including mixtures thereof, and it being possible for parts of the oxyalkylene radical to be substituted by styrene oxide, or are a polyester radical based on, for example, $(C_1$-$C_{18})$hydroxycarboxylic acids or lactones such as β propiolactone, δ-valerolactone, ε-caprolactone or $(C_1$-$C_6)$ alkyl-substituted ε-caprolactone, including mixtures thereof, for example, Y is one or more of the following groups COO, OCO, NHCO, CONH, NHCOO, OOCNH, NHCONH, and a is a number from 1 to 19, and $R^6$ is a $(C_1$-$C_{30})$alkyl, $(C_3$-$C_{22})$alkenyl, hydroxyalkyl, $(C_4$-$C_{13})$cycloalkyl, aryl or $(C_7$-$C_{12})$aralkyl radical, with one or more compounds of the general formula (IX):

$$H_2C=HC—CO—X—R^7—X—CO—CH=CH_2 \qquad (IX)$$

where $R^7$ is a $(C_1$-$C_{18})$alkylene, $(C_3$-$C_{14})$alkenylene, $(C_5$-$C_{12})$cycloalkylene, arylene, $(C_7$-$C_{15})$aralkylene or polyoxyalkylene radical, the oxyalkylene radical being ethylene oxide, propylene oxide or butylene oxide, including mixtures thereof, and it being possible for parts of the oxyalkylene radical to be substituted by styrene oxide, or is a polyester radical based, for example, on $(C_1$-$C_{18})$hydroxycarboxylic acids or on lactones such as β-propiolactone, δ-valerolactone, ε-caprolactone or $(C_1$-$C_6)$alkyl-substituted ε-caprolactone, including mixtures thereof, for example, X is O, NH or $NR^9$, and $R^9$ is $(C_1$-$C_{22})$alkyl, aryl, $(C_7$-$C_{12})$aralkyl, hydroxyalkyl, $(C_5$-$C_{12})$ cycloalkyl radical and subsequently reacting the product, where appropriate (a) with one or more compounds of the general formula (VI):

$$R^5—X—CO—CH=CH_2 \qquad (VI)$$

where $R^5$ is H, a $(C_1$-$C_{22})$alkyl, aryl, $(C_7$-$C_{12})$aralkyl, $(C_5$-$C_{12})$cycloalkyl, hydroxyalkyl, or N,N'-dialkylamino radical, a hydroxyl, $(C_1$-$C_{22})$alkoxy, $(C_5$-$C_{12})$cycloalkoxy, or $(C_7$-$C_{12})$aralkoxypolyoxyalkylene radical, the oxy-alkylene radical being ethylene oxide, propylene oxide or butylene oxide, including mixtures thereof, and it being possible for parts of the oxyalkylene radical to be substituted by styrene oxide, or is a $(C_1$-$C_{22})$-alkanol-, $(C_5$-$C_{12})$cycloalkanol-, $(C_7$-$C_{12})$aralkanol-started or a $(C_1$-$C_{22})$alkoxy-, $(C_5$-$C_{12})$cycloalkoxy-, or $(C_7$-$C_{12})$aralkoxypolyoxyalkylene-started polyester based, for example, on $(C_1$-$C_{18})$hydroxycarboxylic acids or on lactones such as β-propiolactone, δ-valerolactone, ε-caprolactone or $(C_1$-$C_6)$alkyl-substituted ε-caprolactone, including mixtures thereof, for example, X is O, NH or $NR^9$, and $R^9$ is $(C_1$-$C_{22})$alkyl, aryl, $(C_7$-$C_{12})$aralkyl, hydroxyalkyl, $(C_5$-$C_{12})$ cycloalkyl radical and/or (b) one or more compounds of the general formula (VII):

$$R'—NCO \qquad (VII)$$

where R' is $R^8$ or —$C_6H_3(CH_3)$—NHCOO—$R^8$ and $R^8$ is a $(C_1$-$C_{22})$alkyl, aryl, $(C_7$-$C_{12})$aralkyl, or $(C_5$-$C_{12})$-cycloalkyl radical, a $(C_1$-$C_{22})$alkoxy, $(C_5$-$C_{12})$cyclo-alkoxy, or $(C_7$-$C_{12})$ aralkoxypolyoxyalkylene radical, the oxyalkylene radical being ethylene oxide, propylene oxide or butylene oxide, including mixtures thereof, and parts of the oxyalkylene radical being substituted, where appropriate, by styrene oxide, is a $(C_1$-$C_{22})$alkanol-, $(C_5$-$C_{12})$cycloalkanol-, or $(C_7$-$C_{12})$-aralkanol-started or a $(C_1$-$C_{22})$alkoxy-, $(C_6$-$C_{12})$cyclo-alkoxy-, or $(C_7$-$C_{12})$aralkoxypolyoxyalkylene-started polyester based, for example, on $(C_1$-$C_{18})$hydroxy-carboxylic acids or on lactones such as β-propiolactone, δ-valerolactone, ε-caprolactone or $(C_1$-$C_6)$-alkyl-substituted ε-caprolactone, including mixtures thereof, for example.

The compounds of the general formula (IX), if X is O, are preferably diacrylates of linear, branched or cycloaliphatic diols having 2 to 36 C atoms, such as, for example, ethanediol diacrylate, 1,3-butanediol diacrylate, 1,4-butanediol diacrylate, 1,6-hexanediol diacrylate, 1,10-decanediol diacrylate or 2,2-dimethyl-1,3-propanediol diacrylate. Oligo- and polyoxyalkylene diacrylates having 10 to 100 C atoms such as, for example, diethylene glycol diacrylate, triethylene glycol diacrylate, tetraethylene glycol diacrylate, dipropylene glycol diacrylate, tripropylene glycol diacrylate, polyoxyethylene diacrylate, polyoxy-propylene diacrylate, polyoxybutylene diacrylate, polyoxyethylene-polyoxybutylene diacrylate, polyoxy-propylene-polyoxybutylene diacrylate, polyoxyethylene-polyoxypropylene-polyoxyethylene diacrylate are likewise included, as are urethane diacrylate, bisphenol A epoxide diacrylate, ethoxylated and/or propoxylated bisphenol A diacrylate having 1 to 15 alkoxy groups, and ethoxylated or propoxylated 2,2-dimethyl-1,3-propanediol diacrylate. Polyester diacrylates such as, for example, polylactone diacrylates based on caprolactone and/or valerolactone, and mixed polyether-polyester diacrylates, are likewise useful as compounds of the general formula (IX).

Where X is NH it is preferred to use bisacrylamides such as, for example, N,N'-methylenebisacrylamide or N,N'-(1,2-dihydroxyethylene)bisacrylamide. The diacrylates can also be used in mixtures with one another or together with the bisacrylamides, and it is likewise possible to use small amounts of triacrylates such as, for example, trimethylolpropane triacrylate or alkoxylated trimethylolpropane triacrylate.

The addition reaction between the compounds of the general formula (VIII) and (IX) is carried out preferably at a reaction temperature of 60 to 100° C., more preferably of 70 to 90° C. The ratio between the compounds of the general formulae (VIII) and (IX) is preferably selected such that for each mole of compound of the general formula (IX), if $R^1$ in that compound is H, use is made of preferably 1.8 mol to 2.2 mol, more preferably 1.9 mol to 2.1 mol and very preferably 2 mol of compound (VIII). If $R^1$ in the compound of the general formula (IV) is $(CH_2)_2$—CO—X—$R^5$, then preferably 1.8 mol to 2.2 mol, more preferably 1.9 mol to 2.1 mol and very preferably 2 mol of compound (VI) are used per preferably 1 mole of the adduct of the compounds of the general formulae (VIII) and (IX), at a reaction temperature of preferably 60 to 100° C., more preferably 70 to 90° C. The reaction can be carried out with or without solvent. Suitable solvents are all aliphatic, aromatic, protic and aprotic solvents, such as methoxypropyl acetate, cyclohexane, toluene, xylene, higher-boiling aromatics or isoparaffins. N-Methylpyrrolidone or N-ethylpyrrolidone, but also alcohols such as ethanol, propanol, isobutanol or glycols such as butyl glycol, for example, are likewise suitable. Mixtures of solvents can also be used.

Where $R^1$ in the compounds of the general formula (IV) is CONH—R', with R'=$R^8$ or —$C_6H_3(CH_3)$—NHCOO—$R^8$, preferably 1.8 mol to 2.2 mol, more preferably 1.9 mol to 2.1 mol and very preferably 2 mol of the compound of the general formula (VII) is added per preferably 1 mole of the adduct of the compounds of the general formulae (VIII) and (IX), at a reaction temperature of preferably 50 to 100° C., more preferably of 60 to 80° C. The monoisocyanates may be the same or different. This reaction can be carried out with or without catalyst. Suitable catalysts include not only organotin compounds such as DBTL, for example, but also tertiary amines such as DABCO, for example. This reaction can be carried out with or without solvent. Suitable solvents are all aliphatic, aromatic and aprotic solvents such as, for example, methoxypropyl acetate, cyclohexane, toluene, xylene, higher-boiling alkylbenzenes or isoparaffins, N-methylpyrrolidone or N-ethyl-pyrrolidone. Mixtures of solvents can also be used.

The present invention further provides for the use of the amide-containing polymers of the invention, or of the amide-containing polymers obtained by the process of the invention, as rheology control additives, especially in solvent-borne and solvent-free coating materials based on binders such as, for example, polyurethanes (1K and 2K), polyacrylates, polyester resins, alkyd resins and epoxy resins, PVC plastisols and PVC organosols, epoxide-based coatings and unsaturated polyester resins. By coating materials it is also possible to comprehend nail varnishes, of the kind described for example in patent U.S. Pat. No. 6,156,325.

The amount in which the amide-containing polymers of the invention are used is typically 0.05% to 5.0% by weight of active substance, preferably 0.1% to 3.0% by weight of active substance and more preferably 0.2% to 2.0% by weight of active substance, based on the weight of the overall formulation.

The invention further provides cured and uncured polymer compositions comprising one or more of the amide-containing polymers of the invention and/or of the amide-containing polymers obtained by the process of the invention.

EXAMPLES

Example 1

A 1-liter 3-necked flask with stirrer, water separator thermometer is charged in succession with 226.4 g (0.4 mol) of Pripol™ 1006 dimer acid (dimerized fatty acid, hydrogenated, Uniqema), 69.6 g (0.6 mol) of hexamethylenediamine and 127 g of Shellsol A (high-boiling aromatic hydrocarbon, Shell Chemicals) and this initial charge is heated slowly at 170° C. The water which is slowly liberated during the reaction is separated off azeotropically via the water separator. The condensation product possesses an amine number of approximately 54. Thereafter the reaction mixture is cooled to 50° C.

Example 2

A 1-liter 3-necked flask with stirrer, water separator and thermometer is charged in succession with 226.4 g (0.4 mol) of Pripol™ 1006 dimer acid (Uniqema), 55.7 g (0.48 mol) of hexamethylenediamine and 121 g of Shellsol D40 (dearomatized hydrocarbon, Shell Chemicals) and this initial charge is heated slowly at 170° C. The water which is slowly liberated during the reaction is separated off azeotropically via the water separator. The condensation product possesses an amine number of approximately 23. Thereafter the reaction mixture is cooled to 50° C.

Example 3

A 1-liter 3-necked flask with stirrer, water separator and thermometer is charged in succession with 226.4 g (0.4 mol) of Pripol™ 1006 dimer acid (Uniqema), 69.6 g (0.6 mol) of hexamethylenediamine and 152 g of Shellsol D40 and this initial charge is heated slowly at 170° C. The water which is slowly liberated during the reaction is separated off azeotropically via the water separator. The condensation product possesses an amine number of approximately 51. Subsequently 57.6 g (0.2 mol) of tall oil fatty acid (mixture of monocarboxylic acids with a high oleic and linoleic acid content and about 2% of resin acids (abietic acid), Arizona Chemical GmbH) are added and the water which is liberated during this reaction is separated off azeotropically via the water separator. This condensation product possesses an amine number of approximately 23. Thereafter the reaction mixture is cooled to 50° C.

Example 4

A 1-liter 3-necked flask with stirrer, water separator and thermometer is charged in succession with 232 g (0.4 mol) of Pripol™ 1017 dimer acid (dimerized fatty acid, unsaturated, Uniqema), 55.7 g (0.48 mol) of hexa-methylenediamine and 133 g of Cobersol B 60 (isoparaffinic hydrocarbon mixture, C9-C12 isoalkanes, Cölner Benzin-Raffinerie) and this initial charge is heated slowly at 170° C. The water which is slowly liberated during the reaction is separated off azeotropically via the water separator. The condensation product possesses an amine number of approximately 22. Subsequently 22.8 g (0.08 mol) of stearic acid are added and the water which is liberated during this reaction is separated off azeotropically via the water separator. This condensation product possesses an amine number of approximately 10.5. Thereafter the reaction mixture is cooled to 50° C.

Example 5

A 1-liter 3-necked flask with stirrer, water separator and thermometer is charged in succession with 214.5 g (0.375 mol) of Empol® 1062 dimer acid (distilled dimerized fatty acid, partially hydrogenated, Cognis), 68.1 g (0.5 mol) of m-xylylenediamine and 121 g of Cobersol B 60 and this initial charge is heated slowly at 170° C. The water which is slowly liberated during the reaction is separated off azeotropically via the water separator. The condensation product possesses an amine number of approximately 35. Thereafter the reaction mixture is cooled to 50° C.

Example 6

A 1-liter 3-necked flask with stirrer, water separator and thermometer is charged in succession with 146 g (1 mol) of adipic acid, 180 g (1.25 mol) of octamethylenediamine and 140 g of Shellsol A and this initial charge is heated slowly at 170° C. The water which is slowly liberated during the reaction is separated off azeotropically via the water separator.

The condensation product possesses an amine number of approximately 63. Thereafter the reaction mixture is cooled to 50° C.

Example 7

A 500 ml 3-necked flask with stirrer, reflux condenser and thermometer is charged in succession with 150.9 g (0.075 mol) of the condensation product from Example 1 and 17 g (0.15 mol) of N-isopropylacrylamide and this initial charge is heated to 80° C. The reaction mixture is stirred for 3 hours. Then the product is diluted with isobutanol to 40% solids.

Example 8

A 500 ml 3-necked flask with stirrer, reflux condenser and thermometer is charged in succession with 143.4 g (0.03 mol) of the condensation product from Example 2 and 13 g (0.06 mol) of isodecyl acrylate and this initial charge is heated to 80° C. The reaction mixture is stirred for 3 hours. Then the product is diluted with isobutanol to 40% solids.

Example 9

A 500 ml 3-necked flask with stirrer, reflux condenser and thermometer is charged in succession with 143.4 g (0.03 mol) of the condensation product from Example 2 and 16 g (0.06 mol) of polyoxyethylene 200 acrylate (Blemmer® AE 200, NOF) and this initial charge is heated to 80° C. The reaction mixture is stirred for 3 hours. Then the product is diluted with isobutanol to 40% solids.

Example 10

A 500 ml 3-necked flask with stirrer, reflux condenser and thermometer is charged in succession with 143.8 g (0.06 mol) of the condensation product from Example 3 and 15 g (0.03 mol) of polyoxyethylene 400 diacrylate (Sartomer™ 344, Cray Valley) and this initial charge is heated to 80° C. The reaction mixture is stirred for 3 hours. Then the product is diluted with isobutanol to 40% solids.

Example 11

A 500 ml 3-necked flask with stirrer, reflux condenser and thermometer is charged in succession with 143.8 g (0.06 mol) of the condensation product from Example 3 and 4.6 g (0.03 mol) of N,N'-methylenebisacrylamide and this initial charge is heated to 80° C. The reaction mixture is stirred for 3 hours. Then the product is diluted with isobutanol to 40% solids.

Example 12

A 500 ml 3-necked flask with stirrer, reflux condenser and thermometer is charged in succession with 154.97 g (0.03 mol) of the condensation product from Example 4 and 18 g (0.03 mol) of polyoxyethylene 400 acrylate (Blemmer® AE 400, NOF) and this initial charge is heated to 80° C. The reaction mixture is stirred for 3 hours. Then the product is diluted with isobutanol to 40% solids.

Example 13

A 500 ml 3-necked flask with stirrer, reflux condenser and thermometer is charged in succession with 154.97 g (0.03 mol) of the condensation product from Example 4 and 9.7 g (0.03 mol) of stearyl acrylate and this initial charge is heated to 80° C. The reaction mixture is stirred for 3 hours. Then the product is diluted with isobutanol to 40% solids.

Example 14

A 500 ml 3-necked flask with stirrer, reflux condenser and thermometer is charged in succession with 154.97 g (0.03 mol) of the condensation product from Example 4 and 12.5 g (0.03 mol) of lauroxypolyoxyethylene 200 acrylate (Blemmer® ALE 200, NOF) and this initial charge is heated to 80° C. The reaction mixture is stirred for 3 hours. Subsequently 9 g (0.03 mol) of stearyl isocyanate are added and the mixture is stirred at 80° C. for a further 2 hours. Then the product is diluted with isobutanol to 30% solids.

Example 15

A 500 ml 3-necked flask with stirrer, reflux condenser and thermometer is charged in succession with 153.77 g (0.05 mol) of the condensation product from Example 5 and 34.4 g (0.1 mol) of Tone™ M 100 (adduct of hydroxy-ethyl acrylate with 2 mol of $\epsilon$-caprolactone, DOW) and this initial charge is heated to 80° C. The reaction mixture is stirred for 3 hours. Then the product is diluted with isobutanol to 30% solids.

Example 16

A 500 ml 3-necked flask with stirrer, reflux condenser and thermometer is charged in succession with 82.86 g (0.05 mol) of the condensation product from Example 6 and 24 g (0.1 mol) of lauryl acrylate and this initial charge is heated to 80° C. The reaction mixture is stirred for 3 hours. Subsequently 24.8 g (0.1 mol) of the isocyanate prepolymer of the formula $OCN-C_6H_4(CH_3)-NHCOOC_4H_9$ from U.S. Pat. No. 6,420,466 are added and the mixture is stirred at 80° C. for a further 2 hours. Then the product is diluted with isobutanol to 30% solids.

Use Examples

White paint formula: Degalan white paint, 28% binder, 20% $TiO_2$

| | |
|---|---:|
| Degalan ® LP 64/12, 35% in Shellsol A (thermoplastic acrylate, 35% dilution in Shellsol A, Röhm GmbH) | 34.4 |
| Disperbyk ® 110 | 0.6 |
| Kronos 2160 ($TiO_2$) | 20 |
| Dispersion: 30 min. Dispermat, 40° C., 18 m/s peripheral speed (8000 rpm 4.5 cm Teflon disc) glass beads 1 mm 1:1 with millbase | |
| Degalan ® LP 64/12, 35% in Shellsol A | 45 |
| | 100 |

Additive dosing: 1% by weight of active substance, based on the weight of the overall composition Incorporation: Add additive with stirring using the Dispermat, toothed disc 2.5 cm, 1000 rpm, 2 min.

Testing: Test of rheological activity in the form of the sag limit.

For this purpose the additized paint systems are applied using the stepped coater 50-500 μm and 550-1000 μm to BYK Gardner 2801 contrast charts, using an automatic applicator from BYK Gardner (rate: 3 cm/sec). The contrast charts are dried in vertical suspension. The stability is read off wet in μm. This is a measure of the rheological activity. The results are set out in Table 1.

TABLE 1

| Additive | Sag limit [μm] |
|---|---|
| Control (no additive) | 90 |
| Example 7 | 700 |
| Example 8 | 900 |
| Example 9 | 850 |
| Example 10 | 850 |
| Example 11 | 1000 |
| Example 12 | 600 |
| Example 13 | 900 |
| Example 14 | 650 |
| Example 15 | 650 |
| Example 16 | 550 |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. Amide-containing polymers of the general formula (I)

$$R^5-O-CO-(CH_2)_2-NH-R^2-(NH-CO-R^3-CO-NH-R^4)_a-NH-(CH_2)_2-CO-OR^5 \quad (I)$$

or their salts with carboxylic acids, phosphoric esters or sulphonic acids, wherein a is a number from 1 to 19, $R^2$, $R^3$, and $R^4$ are a $(C_1-C_{40})$alkylene, and $R^5$ is a $(C_1-C_{22})$alkyl or alkoxypolyoxyalkylene.

2. Amide-containing polymers of the general formula (I)

$$R^5-O-CO-(CH_2)_2-NH-R^2-(NH-CO-R^3-CO-NH-R^4)_a-Y-R^6 \quad (I)$$

or their salts with carboxylic acids, phosphoric esters or sulphonic acids,
wherein a is a number from 1 to 19, $R^2$, $R^3$, and $R^4$ are a $(C_1-C_{40})$alkylene, $R^5$ is a $(C_1-C_{22})$alkyl or alkoxypolyoxyalkylene, $R^6$ is a $(C_1-C_{30})$alkyl, and Y is —NH—CO—.

3. Amide-containing polymers of the general formula (I)

$$R^5-O-CO-(CH_2)_2-NH-R^2-(NH-CO-R^3-CO-NH-R^4)_a-NH-(CH_2)_2-CO-OR^5 \quad (I)$$

$$R^5-O-CO-(CH_2)_2-NH-R^2-(NH-CO-R^3-CO-NH-R^4)_a-Y-R^6 \quad (I)$$

or their salts with carboxylic acids, phosphoric esters or sulphonic acids,
wherein a is a number from 1 to 19, $R^2$, $R^3$, and $R^4$ are a $(C_1-C_{40})$alkylene, $(C_3-C_{40})$alkenylene, $(C_5-C_{40})$cycloalkylene, arylene, $(C_7-C_{40})$aralkylene or polyoxyalkylene radical or a polyester radical, $R^5$ is $(C_1-C_{22})$alkyl, or alkoxypolyoxyalkylene, Y is —NH—CO—, and $R^6$ is a $(C_{12}-C_{30})$alkyl or a $(C_3-C_{22})$alkenyl radical.

4. Amide-containing polymers according to claim 3, wherein if one or more of the radicals $R^2$, $R^3$, $R^4$, or $R^5$ contain a polyoxyalkylene fraction, this or these radicals are constructed from ethylene oxide, propylene oxide, butylene oxide units or a combination thereof, in random or blockwise arrangement, and, optionally, one or more of the ethylene oxide, propylene oxide or butylene oxide units are substituted by styrene units.

5. Amide-containing polymers according to claim 3, wherein a is a number from 1 to 19, $R^2$ and $R^4$ independently of one another are a $(C_2-C_{18})$ alkylene, or $(C_7-C_{15})$aralkylene radical, $R^3$ is a $(C_2-C_{40})$alkylene, $(C_3-C_{40})$alkenylene, $(C_5-C_{40})$cycloalkylene, arylene, or $(C_7-C_{40})$aralkylene radical, $R^5$ is $(C_1-C_{22})$alkyl, or alkoxypolyoxyalkylene, and $R^6$ is a $(C_{12}-C_{30})$alkyl, or a $(C_{12}-C_{22})$alkenyl radical.

6. Amide-containing polymers according claim 3, wherein a is a number from 2 to 7, $R^2$ and $R^4$ independently of one another are a $(C_2-C_{12})$ alkylene, or $(C_7-C_{12})$aralkylene radical, $R^3$ is a $(C_2-C_{40})$alkylene, $(C_3-C_{40})$alkenylene, $(C_5-C_{40})$cycloalkylene, arylene, or $(C_7-C_{40})$aralkylene radical, $R^5$ is $(C_1-C_{22})$alkyl, or alkoxypolyoxyalkylene, and $R^6$ is a $(C_{12}-C_{20})$alkyl radical or a $(C_{12}-C_{20})$alkenyl radical.

7. Amide-containing polymers according to claim 3, wherein a is a number from 2 to 7, $R^2$ and $R^4$ independently of one another are a $(C_2-C_8)$ alkylene, or $(C_7-C_9)$aralkylene radical, $R^3$ is a $(C_{30}-C_{40})$alkylene, $(C_{30}-C_{40})$alkenylene, $(C_{30}-C_{40})$ cycloalkylene, arylene, or $(C_{30}-C_{40})$aralkylene radical, $R^5$ is $(C_1-C_{22})$alkyl, or alkoxypolyoxyalkylene, and $R^6$ is a $(C_{12}-C_{20})$alkyl radical or a $(C_{12}-C_{20})$alkenyl radical.

* * * * *